United States Patent
Dimmig et al.

Patent Number: 5,412,140
Date of Patent: May 2, 1995

[54] METAL-FREE DITHIOPHOSPHORIC ACID DERIVATIVES

[75] Inventors: Thomas Dimmig, Jena; Gunter Jäger, Freyburg; Thomas Petri, Jena; Wolfram Radig, Apolda; Günther Schilling, Schwetzingen; Jürgen Braun, Speyer; Volker Schäfer, Altrip, all of Germany

[73] Assignee: Rhein Chemie Rheinau GmbH, Mannheim, Germany

[21] Appl. No.: 165,424

[22] Filed: Dec. 6, 1993

[30] Foreign Application Priority Data

Dec. 16, 1992 [DE] Germany .......... 42 42 502.6

[51] Int. Cl.$^6$ .......... C07F 9/40
[52] U.S. Cl. .......... 558/208; 558/209; 558/210; 568/15
[58] Field of Search .......... 568/15; 558/208, 209, 558/210

[56] References Cited

U.S. PATENT DOCUMENTS

| | | | |
|---|---|---|---|
| 2,291,086 | 1/1960 | McCall et al. | 260/161 |
| 4,171,357 | 10/1979 | Theobald et al. | 558/208 |
| 5,057,235 | 10/1991 | Farng et al. | 558/208 |

FOREIGN PATENT DOCUMENTS 0049222  4/1982  European Pat. Off. .

OTHER PUBLICATIONS

Orbit Abstract of EP-0-049 222, C82-E29083, Feb. 1982.
Chemical Abstracts 105:227012r(Musaeva et al), Jun. 1986.
Chemical Abstracts 98:142922z(Belov et al), Sep. 1983.

*Primary Examiner*—Johann Richter
*Assistant Examiner*—Michael B. Hydorn
*Attorney, Agent, or Firm*—Connolly & Hutz

[57] ABSTRACT

Alkyl glycidol ether/dithiophosphoric acid addition products corresponding to the following general formula:

$$[R^1]O[C(H)(H)][C(H)C(H)(H)(OH)(R^4)] \quad (I)$$

in which
  $R^4 = [(R^2O)(R^3O)]P(S)S$,
  $R^1 \ldots R^3 =$ alkyl, aryl,
  a process for the production of the adducts from the corresponding dithiophosphoric acids and glycidol ethers and the use of the addition products as lubricant additives in lubricants based on mineral oils or native oils.

4 Claims, No Drawings

METAL-FREE DITHIOPHOSPHORIC ACID DERIVATIVES

This invention relates to metal-free dithiophosphoric acid derivatives based on glycidol ethers, to their production and to their use.

Metal dithiophosphates have long been successfully used as lubricant additives, above all for improving the anti-wear properties and resistance to ageing of mineral oils. Zinc dithiophosphates have proved to be particularly effective in this regard. However, they do not meet all the requirements which, in addition to those mentioned, an additive is expected to satisfy as a constituent of lubricants for modern machines. Thus, all metal dithiophosphates are so-called ash formers which can produce troublesome deposits on the lubricated friction elements. In addition, metal ions can delay the often desirable rapid biological degradation of the blended lubricants.

There has been no shortage of attempts to produce so-called ash-free (metal-free) dithiophosphates which would not have any of the disadvantages mentioned above. For example, efforts have been made to neutralize dithiophosphoric acids by addition onto unsaturated hydrocarbons. However, the reactions are incomplete, the reaction products are only partly soluble in the usual basic oils and lead to a deterioration in their ageing resistance. In addition, metal-free dithiophosphates, for example, have been developed by reaction of dithiophosphoric acids—produced from sulfurized alcohols and $P_4S_{10}$—with epoxidized oligomeric propylene and have been proposed as corrosion inhibitors by virtue of their specific properties.

The problem addressed by the present invention was to find derivatives of dithiophosphoric acids which would be metal-free and readily soluble in the usual basic oils, would improve the anti-wear properties and resistance to ageing of the basic oils and would be comparable with zinc dithiophosphates in their effectiveness based on these properties.

According to the invention, this problem has been solved by dithiophosphoric acid derivatives of epoxidized hydrocarbons ether-bridged in the carbon chain.

Accordingly, the present invention relates to addition products of glycidol ethers and dithiophosphoric acids differing in the structure of their alkyl, aryl or mixed alkyl/aryl groups.

Suitable glycidol ethers are, for example, 2-ethylhexyl glycidol ether or n-octyl glycidol ether. Suitable dithiophosphoric acids are, for example, O,O'-dialkyl, O,O'-diaryl or O,O'-alkyl/aryl dithiophosphoric acids of which the alkyl groups may be branched or unbranched and of which the aryl groups may be alkylated.

According to the invention, the problem, stated above has been solved by a process for the production of metal-free dithiophosphoric acid derivatives in which glycidol ether or dithiophosphoric acid is introduced into a stirred reactor and dithiophosphoric acid or glycidol ether is slowly added so that the exothermic chemical reaction thus initiated takes place at a reaction temperature only slightly above room temperature.

The present invention also relates to the production of the addition products of alkyl glycidol ethers and dithiophosphoric acids. The two components mentioned may be smoothly and completely reacted in a molar ratio of 1:1 at temperatures just above room temperature. The reaction is exothermic and may readily be controlled by addition of one component in portions to the other component.

According to the invention, the solution to this problem is characterized in that the metal-free dithiophosphoric acid derivatives formed by reaction of glycidol ethers with dithiophosphoric acids are dissolved in the basic oil of a lubricant—consisting of a mineral oil or a natural oil—and improve the anti-wear properties and the resistance to ageing of the basic oil.

The present invention also relates to the use of the described addition compounds to improve the properties of lubricants based on mineral oils or native oils. The addition compounds are readily soluble in the basic liquids and show anti-wear and anti-ageing activity in the usual tests.

The invention is illustrated by the following Example.

EXAMPLE 1

The Example shows a metal-free dithiophosphoric acid derivative obtained by reaction of 2-ethylhexyl glycidol ether with an O,O'-dialkyl dithiophosphoric acid in accordance with the following equation:

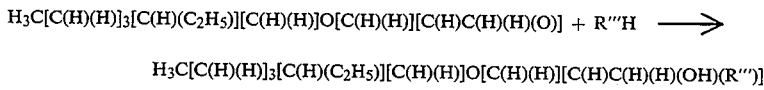

in which
$R''' = [(R'O)(R''O)]P(S)S$,
$R'$, $R''$ = alkyl, aryl

The process for the production of metal-free dithiophosphoric acid derivatives under laboratory conditions is described by way of example in the following:

470 g (2.5 mol) 2-ethylhexyl glycidol ether are introduced into a 2-liter three-necked flask equipped with a stirrer, reflux condenser, internal thermometer and dropping funnel. 675 g (2.5 mol) mixed $C_3C_4C_8$ dithiophosphoric acid ($C_3$: isopropyl; $C_4$: isobutyl; $C_8$: 2-ethylhexyl) are then slowly added dropwise at 30 to 40° C. (highly exothermic reaction) so that the reaction temperature remains constant. After all the acid has been added, the reaction mixture is stirred for 2 hours at 30° to 40° C. The clear light yellow liquid formed has a viscosity of 21.9 mm²/s (40° C.), a density of 1.0066 g/cm³ (20° C.) and a refractive index of 1.4820 (20° C.) and dissolves readily in refined rapeseed oil/colza oil or mineral oil (paraffin-based).

Performance testing of the product in the laboratory for its anti-wear properties and resistance to ageing produced the following results:

| Lubricant | Test methods VKA[1] | FZG[2] | Rotary bomb test[3] |
|---|---|---|---|
| Colza oil/rapeseed oil | 0.70 | 10 | 6 |
| Mineral oil | 1.0 | n.d. | 30 |
| Product in colza oil | 0.40[4] | n.d. | n.d. |
| Product in mineral oil | 0.45[4] | 12[4] | 138[5] |

-continued

| Lubricant | Test methods VKA[1)] | FZG[2)] | Rotary bomb test[3)] |
|---|---|---|---|
| ZN-DTP in mineral oil | 0.5[4)] | 12[4)] | 116[5)] |

[1)]Four-ball apparatus
Test period: 1 h
Test force 300 N
Measured: wear mark diameter (mm)
[2)]FZG test
Measured: load stage reached
[3)]Test for ageing resistance
Measured: incubation time (mins.)
[4)]1% additive in oil
[5)]Weight of additive in oil adjusted to 1% phosphorus in oil.

The results reflect the increase in the protection against wear (VKA), load bearing capacity (FZG) and ageing resistance (rotary bomb test) of natural or mineral basic oils by using the products according to the invention as additives.

The Example demonstrates the suitability of the metal-free dithiophosphoric acid derivatives according to the invention as additives in natural and mineral oils.

We claim:

1. Metal-free dithiophosphoric acid derivatives, corresponding to the following general formula

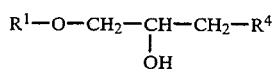   (I)

wherein

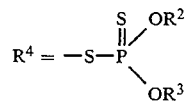

and
$R^1$ = an alkyl or aryl group and either $R^2$ or $R^3$ is an alkyl group and the other is an aryl group.

2. The metal-free dithiophosphoric acid derivatives of claim 1, wherein either $R^2$ or $R^3$ is a branched alkyl group and the other is an aryl group.

3. The metal-free dithiophosphoric acid derivatives of claim 1, wherein either $R^2$ or $R^3$ is an alkyl group and the other is an alkylated aryl group.

4. Metal-free dithiophosphoric acid derivatives, corresponding to the following general formula

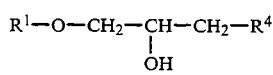   (I)

wherein

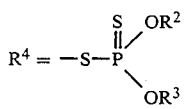

and
$R^1$ = an alkyl or aryl group and $R^2$ and $R^3$ are both alkyl groups wherein one or both of $R^2$ and $R^3$ is a branched alkyl group.

* * * * *

UNITED STATES PATENT AND TRADEMARK OFFICE
CERTIFICATE OF CORRECTION

PATENT NO. : 5,412,140
DATED : May 2, 1995
INVENTOR(S) : Dimmig et al.

It is certified that error appears in the above-indentified patent and that said Letters Patent is hereby corrected as shown below:

On the cover page, in the References Cited section, U.S. PATENT DOCUMENTS subsection, patent number "2,291,086" should be --2,921,086--.

Signed and Sealed this

Twenty-first Day of May, 1996

*Attest:*

BRUCE LEHMAN

*Attesting Officer*  *Commissioner of Patents and Trademarks*